(12) United States Patent
Petralia et al.

(10) Patent No.: US 12,059,518 B2
(45) Date of Patent: Aug. 13, 2024

(54) DEVICE FOR THE CONTINUOUS MONITORING OF BLOOD CHARACTERISTIC QUANTITIES IN AN EXTERNAL CARDIOVASCULAR SUPPORTING CIRCUIT

(71) Applicant: EUROSETS S.R.L., Medolla (IT)

(72) Inventors: Antonio Petralia, Medolla (IT); Nicola Ghelli, Medolla (IT); Mirko Belliato, Medolla (IT)

(73) Assignee: EUROSETS S.R.L., Medolla (IT)

( * ) Notice: Subject to any disclaimer, the term of this patent is extended or adjusted under 35 U.S.C. 154(b) by 1051 days.

(21) Appl. No.: 16/965,408

(22) PCT Filed: Feb. 6, 2019

(86) PCT No.: PCT/IB2019/050934
§ 371 (c)(1),
(2) Date: Jul. 28, 2020

(87) PCT Pub. No.: WO2019/155365
PCT Pub. Date: Aug. 15, 2019

(65) Prior Publication Data
US 2020/0353146 A1    Nov. 12, 2020

(30) Foreign Application Priority Data
Feb. 7, 2018 (IT) .................. 102018000002461

(51) Int. Cl.
*A61M 1/16* (2006.01)
*A61M 1/36* (2006.01)

(52) U.S. Cl.
CPC ........ *A61M 1/1698* (2013.01); *A61M 1/3609* (2014.02); *A61M 1/3666* (2013.01); *A61M 2205/3334* (2013.01); *A61M 2205/502* (2013.01); *A61M 2230/202* (2013.01); *A61M 2230/205* (2013.01)

(58) Field of Classification Search
CPC .............. A61M 1/1698; A61M 1/3609; A61M 1/3666; A61M 2205/3334; A61M 2205/502; A61M 2230/202; A61M 2230/205; A61M 2230/432
See application file for complete search history.

(56) References Cited

U.S. PATENT DOCUMENTS 5,810,759 A    9/1998 Merz

FOREIGN PATENT DOCUMENTS

| EP | 2 455 116 B1 | 4/2016 |
| WO | WO 2007/075089 A1 | 7/2007 |
| WO | WO 2016/180953 A1 | 11/2016 |

*Primary Examiner* — Leslie R Deak
(74) *Attorney, Agent, or Firm* — ASLAN LAW, P.C.

(57) ABSTRACT

A device for the continuous monitoring of blood characteristic quantities in an external cardiovascular supporting circuit, said circuit including a venous line which conveys blood from the patient to an oxygenator, and along which at least one pump is arranged, and an arterial line which returns blood from the oxygenator to the patient, where said oxygenator comprises at least one blood inlet port connected to said venous line and at least one blood outlet port connected to said arterial line, at least one inlet channel and at least one outlet channel of a work gas intended to supply oxygen to the blood and/or to remove carbon dioxide from the same.

10 Claims, 2 Drawing Sheets

DEVICE FOR THE CONTINUOUS MONITORING OF BLOOD CHARACTERISTIC QUANTITIES IN AN EXTERNAL CARDIOVASCULAR SUPPORTING CIRCUIT

CROSS-REFERENCE TO RELATED APPLICATIONS

This application is a National Stage Entry of PCT/IB2019/050934 filed on Feb. 6, 2019. This application claims priority to IT Patent Application No. 102018000002461 filed on Feb. 7, 2018, and to PCT Application No. PCT/IB2019/050934 filed on Feb. 6, 2019, the entire contents of which are hereby incorporated by reference.

TECHNICAL FIELD

The present invention relates to a device for the continuous monitoring of blood characteristic quantities in an external cardiovascular supporting circuit.

BACKGROUND ART

It is well known that during cardiac surgery an extracorporeal blood circulation is established with the main purpose of perfusion of vital organs, i.e. their spraying with oxygenated blood, to ensure their correct function, and for this purpose one of the appliances comprised in the extracorporeal circuit consists of an oxygenator in which the blood coming from the venous line taken from the patient is enriched with oxygen before being introduced into the arterial line of return to the patient.

In particular, for example in the case of patients with acute heart and/or respiratory failure, it is possible to support the function of the patient's organs by means of an external circuit. Such external circuit is therefore designed to support the patient's vital functions from a cardiovascular point of view. In other words, part of the blood is naturally oxygenated by the patient's heart and part by the external supporting circuit.

This cardiovascular supporting therapy is called ECMO (ExtraCorporeal Membrane Oxygenation) or ECLS (Extracorporeal Life Support).

In order to control the functioning of the system, consisting of the patient and the external supporting circuit, in order to avoid an insufficient supply of oxygen to the tissues, frequent samples are currently taken of arterial and venous blood, which are directly analyzed in the operating theatre, but it has been shown that this method is not able to provide reliability regarding the state of perfusion of the patient.

Also known are systems for monitoring blood characteristics provided with a microprocessor able to receive data measured by sensors and/or inputted by operators and process them to provide the aforementioned blood characteristics. However, these systems are also deficient, as they are not able to provide sufficient information to medical staff to provide them with a complete and exhaustive picture of the patient's condition and of the functioning of the external supporting circuit.

A monitoring system of known type is described by WO 2016/180953A1, which comprises a microprocessor provided with means adapted to calculate the quantity relating to the amount of carbon dioxide removed by the oxygenator $V'CO_2ML$ and the quantity relating to the amount of oxygen transferred by the oxygenator $V'O_2ML$.

DESCRIPTION OF THE INVENTION

The aim of the present invention is therefore to provide for a device for the continuous monitoring of blood characteristic quantities in an external cardiovascular supporting circuit, providing the operators with information able to fully guide the same during the interventions for an optimal outcome.

Within this aim, one object of the present invention is to enable the medical staff to effectively monitor the patient's vital functions and, consequently, to adjust the characteristic parameters of the circuit accordingly.

One object of the present invention is to provide the medical staff with information in both numerical and graphical form, so as to enable them to identify and evaluate immediately and intuitively the operation of the device and the patient's vital capacities.

Another object of the present invention is to devise a device for the continuous monitoring of blood characteristic quantities in an external cardiovascular supporting circuit that allows overcoming the mentioned drawbacks of the prior art within a simple, rational, easy, effective to use and low cost solution.

The above mentioned objects are achieved by the present device for the continuous monitoring of blood characteristic quantities in an external cardiovascular supporting circuit according to claim 1.

BRIEF DESCRIPTION OF THE DRAWINGS

Other characteristics and advantages of the present invention will be more evident from the description of a preferred, but not exclusive, embodiment of a device for the continuous monitoring of blood characteristic quantities in an external cardiovascular supporting circuit, illustrated by way of an indicative, but not limited example, in the attached tables of drawings wherein.

EMBODIMENTS OF THE INVENTION

Figure 1:
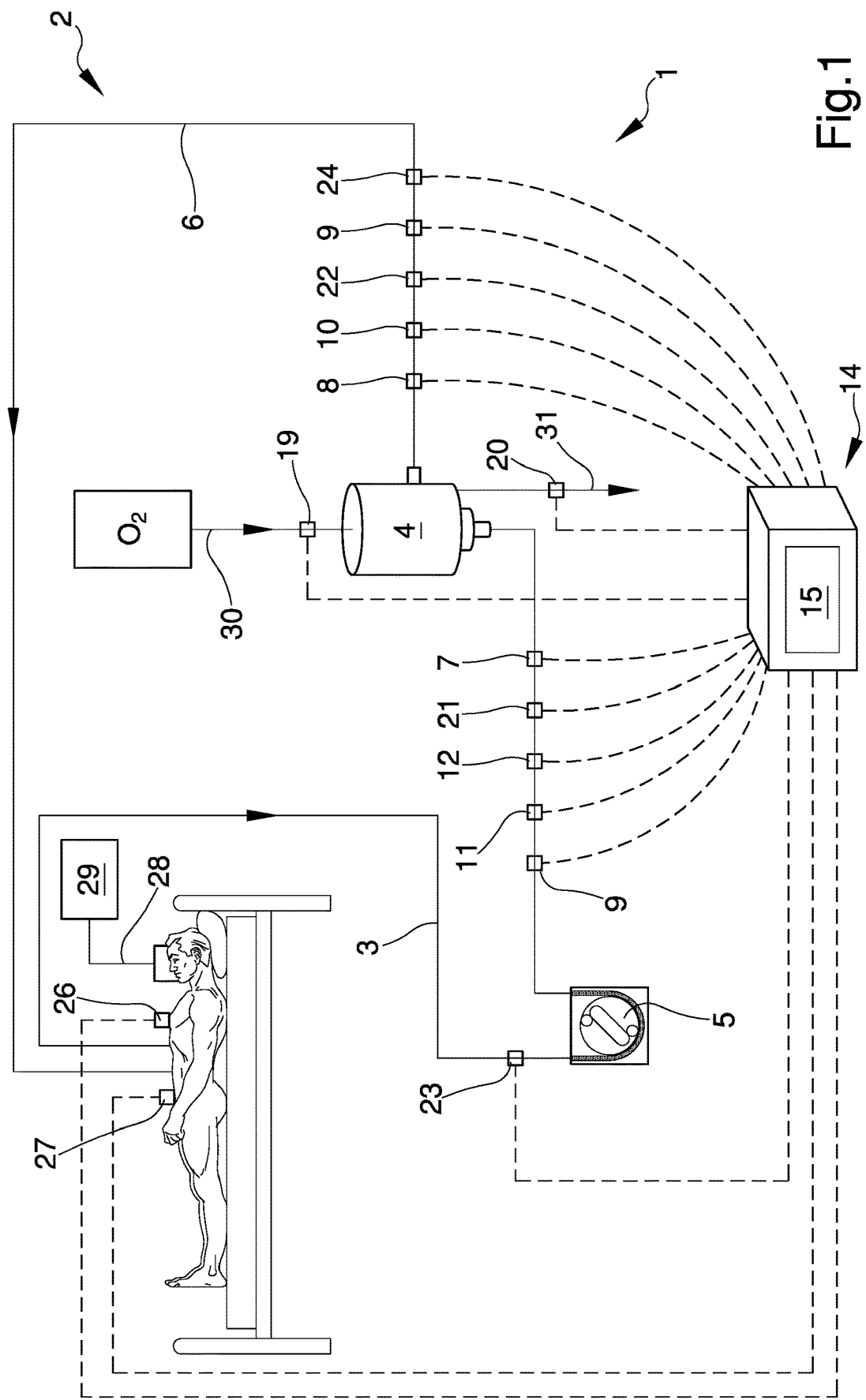
FIG. 1 is a schematic representation of a monitoring device according to the invention.
Figure 2:
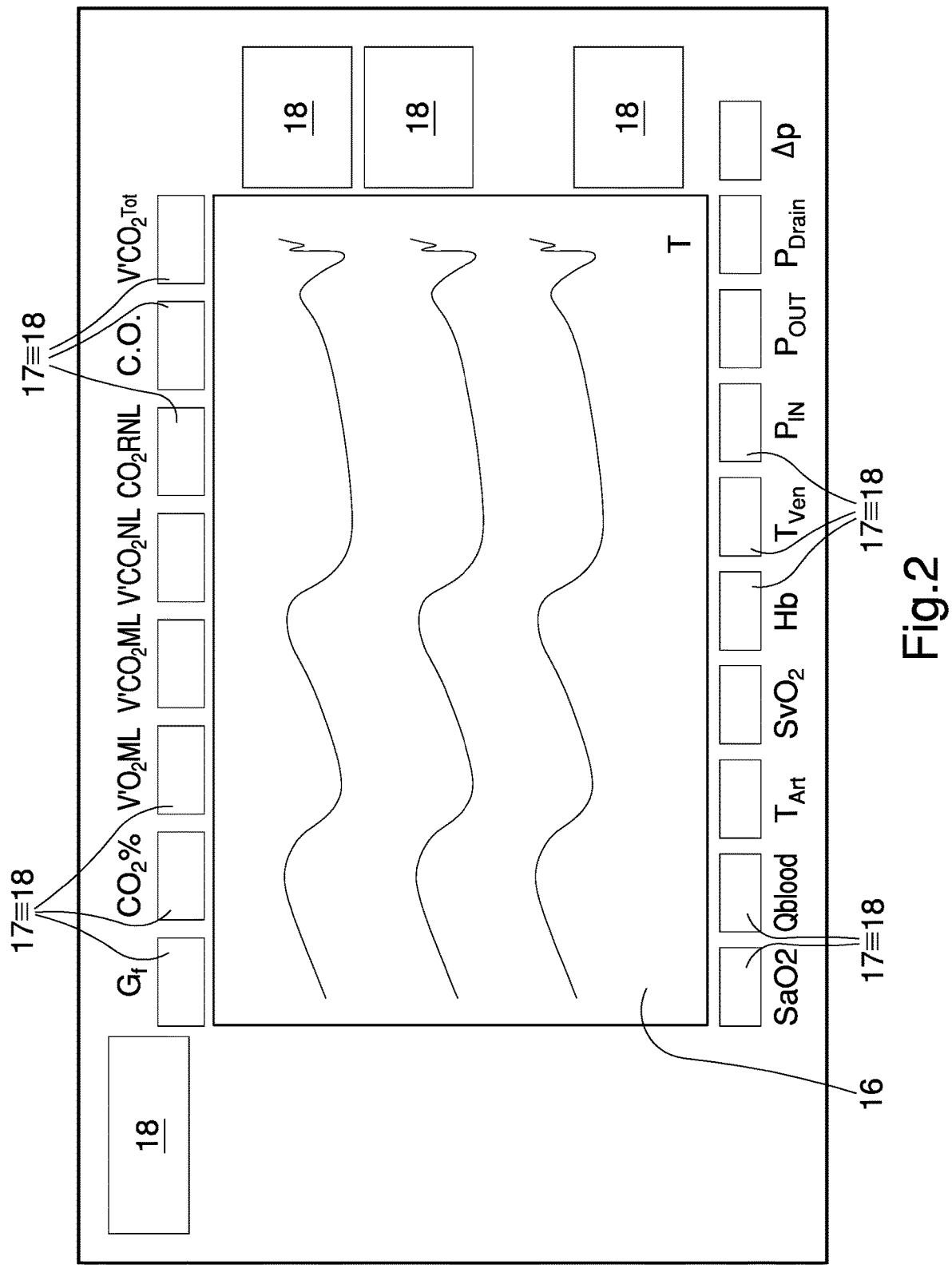
FIG. 2 is a schematic representation of the display of a monitoring device according to the invention.

With particular reference to these illustrations, reference numeral 1 globally indicates a device for the continuous monitoring of blood characteristic quantities in an external cardiovascular supporting circuit.

The circuit, identified in FIG. 1 with reference numeral 2, for example used in ECMO, ECLS or CPB (Cardiopulmonary Bypass) treatments, comprises a venous line 3 which conveys blood from the patient to an oxygenator 4, and along which at least one pump 5 is arranged, and an arterial line 6 which returns blood from the oxygenator 4 to the patient. As is well known, in ECMO and ECLS treatments, the circuit 2 supports the functions of the patient, and so operates together with him/her, while in CPB treatments the circuit 2 completely replaces the functions of the patient, who therefore makes no contribution to the removal of carbon dioxide from the blood.

The oxygenator 4 comprises at least one blood inlet port connected to the venous line 3 and at least one blood outlet port connected to the arterial line 6, at least one inlet channel 30 and at least one outlet channel 31 of a work gas intended to supply oxygen to the blood and/or to remove carbon dioxide from the same.

A ventilation line is also provided, identified in FIG. 1 with reference numeral 28, connected to a pulmonary ventilator 29 adapted to mechanically assist the patient's breathing.

The device 1 comprises one sensor 7 connected to the venous line 3 and one sensor 8 connected to the arterial line 6, suitable for the continuous measurement of the quantities consisting of venous saturation $SvO_2$ of oxygen and of arterial saturation $SaO_2$ of oxygen, respectively. The sensors 7 and 8 can also be defined venous saturation sensor and arterial saturation sensor, respectively.

Preferably, the sensor 7 is inserted at the input connector of the venous line 3 in the oxygenator 4, while the sensor 8 is inserted at the output connector of the arterial line 6 from the oxygenator 4.

Appropriately, along the venous line 3 and along the arterial line 6 are inserted, respectively, a sensor 9 adapted to detect the temperature of the venous blood $T_{Ven}$ and a sensor 10 adapted to detect the temperature of the arterial blood $T_{Art}$. The sensors 9 and 10 can also be defined venous temperature sensor and arterial temperature sensor, respectively.

The device 1 also comprises at least one sensor 11 inserted along the venous line 3 and suitable for the continuous measurement of the quantity constituted by the flow of blood $Q_b$ sent by the pump 5 to the oxygenator 4. The sensor 11 can also be defined: blood flow sensor.

At least one sensor 12 is also provided which is inserted in a point of the external cardiovascular supporting circuit 2 and suitable for the measurement of the quantity constituted by the hemoglobin Hb. The sensor 12 can also be defined: hemoglobin sensor.

The device 1 is further provided with means adapted to enter data by the operator, not shown in details in the illustrations, of an electronic control unit 14 provided with a microprocessor 15 and operationally connected to a display 16. As easily understood, the means for entering data are of the type of buttons.

The microprocessor 15 is adapted to receive the data measured by the sensors 7, 8, 9, 10, 11, 12 and the data entered by the operator to make them appear at least partially on the display 16.

The microprocessor 15 is programmed to display in numerical form on the display 16 the values of all the measured and calculated quantities and in graphic form at least some of such values.

The numerical values of the various measured or entered quantities are shown inside the relative boxes, identified in the illustrations with reference numeral 17.

Appropriately, navigation buttons 18 are also provided which allow the operator to move among a plurality of available screen pages and choose which quantities to display and in what graphic and/or numerical form.

Preferably, the display 16 is of the touch-screen type and some of the navigation buttons 18 correspond to the boxes 17 inside which the numerical values of the measured or calculated quantities appear; by selecting such boxes 17 it is possible to view the graphic trend of such quantities over time.

According to the invention, the device 1 comprises at least one sensor 19 inserted along the inlet channel 30 and suitable for the continuous measurement of the flow of work gas $G_f$, at least one capnometer 20 inserted along the outlet channel 31 and adapted to measure the concentration of carbon dioxide removed from the venous blood, marked as $CO_2\%$. The sensor 19 can also be defined: sensor of the flow of work gas.

Still according to the invention, the microprocessor 15 is provided with means adapted to calculate the quantity relating to the amount of carbon dioxide removed by the oxygenator 4, marked as $V'CO_2ML$, and the quantity relating to the amount of oxygen transferred by the oxygenator 4, marked as $V'O_2ML$. $V'O_2ML$, relating to the amount of oxygen transferred by the oxygenator 4, is calculated according to the following formula:

$$V'O_2ML = Qb \times CaO_2 - CvO_2 \times 10$$

wherein the quantity Qb relating to the flow of blood conveyed by the pump 5 to the oxygenator 4 is detected by the sensor 11 and wherein the quantities $CaO_2$ and $CvO_2$ relating to the arterial and venous oxygen content, respectively, are calculated according to the following formulas:

$$CaO_2 = 0.0138 \times Hb \times SaO_2$$

$$CvO_2 = 0.0138 \times Hb \times SvO_2$$

where the quantities Hb, $SaO_2$ and $SvO_2$ correspond to the hemoglobin, detected by the sensor 12, to the arterial saturation, detected by the sensor 8 and to the venous saturation detected by the sensor 7, respectively.

The quantity $V'O_2ML$ is generally expressed in ml/min $V'CO_2ML$, relating to the amount of carbon dioxide removed by the oxygenator 4, is calculated according to the following formula:

$$V'CO_2ML = CO_2\% \times Gf \times 10$$

where the quantity $CO_2\%$ corresponds to the percentage of oxygen detected by the capnometer 20 and the quantity $G_f$ to the flow of work gas detected by the sensor 19.

The quantity $V'CO_2ML$ is generally expressed in ml/min.

Advantageously, the device 1 comprises manual and/or automatic acquisition means for acquiring the quantity relating to the amount of carbon dioxide removed from the patient's lung, marked as $V'CO_2NL$ and the microprocessor is provided with means adapted to calculate the quantity relating to the amount of total removed carbon dioxide, identified as $V'CO_{2total}$. More particularly, the amount of total removed carbon dioxide $V'CO_{2total}$ corresponds to the sum of the $V'CO_2ML$, relating to the amount of carbon dioxide removed by the oxygenator 4, and of the $V'CO_2NL$, relating to the amount of carbon dioxide removed from the patient's lung.

$$V'CO_{2total} = V'CO_2ML + V'CO_2NL$$

The continuous calculation of the $V'CO_2NL$, and therefore of the $V'CO_{2total}$, enables the medical staff to effectively monitor the patient's vital functions and, therefore, consequently, to regulate the characteristic parameters of the circuit 2. In particular, depending on the patient's ability to supply oxygen to the blood and to remove carbon dioxide, the medical staff adjusts the circuit 2, for example by increasing or decreasing the flow of the work gas $G_f$ which passes through the oxygenator 4. This is because the circuit 2 is meant to support the patient's cardiovascular abilities, so when the patient's functions improve, it is advisable to reduce the contribution provided by the oxygenator 4 and vice versa, in order to provide the correct amount of oxygen to the blood. Preferably, the microprocessor 15 comprises means adapted to calculate the quantity relating to the ratio between the amount of carbon dioxide removed from the patient's lung V'CO$_2$NL and the quantity relating to the amount of total removed carbon dioxide V'CO$_{2total}$. This ratio is marked as CO$_2$RNL.

$$CO_2RNL = V'CO_2NL/V'CO_{2total}$$

Advantageously, the circuit 2 comprises acquisition means for acquiring the quantity relating to the flow rate of blood supplied by the patient, identified as C.O. (Cardiac Output). The C.O. quantity corresponds to the volume of blood emitted by the heart ventricle at each beat (called pulsatory output or stroke), and identified by the acronym SV, multiplied by the heart rate (HR), according to the formula:

$$C.O. = SV \times HR$$

The flow rate of blood supplied by the patient therefore corresponds to the amount of blood which the heart pumps in one minute.

The aforementioned acquisition means, i.e. those relating to the amount of carbon dioxide removed from the patient's lung V'CO$_2$NL and those relating to the flow rate of blood supplied by the patient C.O. are selected from the group comprising: the data entering means and automatic detection means. More particularly, the automatic detection means for automatically detecting the amount of carbon dioxide removed from the patient's lung V'CO$_2$NL correspond to the pulmonary ventilator 29, while the automatic detection means for automatically detecting the flow rate of blood supplied by the patient C.O. comprise a sensor 26 positioned on the patient.

In other words, the figures relating to the amount of carbon dioxide removed from the patient's lung V'CO$_2$NL and to the flow rate of blood supplied by the C.O. patient can be entered manually by the medical staff using the data entering means or can be automatically detected by means of the pulmonary ventilator 29 and the sensor 26, respectively, positioned on the patient him/herself.

Preferably, the microprocessor 15 is also provided with means adapted to calculate the quantity known by the acronym DO$_2$, relating to the amount of conveyed oxygen, the quantity known by the acronym VO$_2$, relating to the amount of oxygen consumed at tissue level, and the quantity known by the acronym O$_2$ER, relating to the oxygen extraction fraction.

More in particular:
the amount of conveyed oxygen DO$_2$ is calculated according to the following formula:

$$DO_2 = C.O. \times Hb \times 1.34 \times SaO_2 + K$$

wherein, we recall, the sensors have provided the data relating to C.O., Hb, SaO$_2$, and wherein K represents a constant value representing the difference between the pressure of the oxygen in the arterial and venous lines.
the amount of oxygen consumed at tissue level VO$_2$ is calculated according to the formula:

$$VO_2 = C.O. \times [Hb \times 1.34 \times SaO_2 + K - Hb \times 1.34 \times SvO_2 + K]$$

wherein the sensors have provided the data relating to C.O., Hb, SaO$_2$, SvO$_2$, and wherein K represents a constant value according to what has been specified above.

O2ER, oxygen extraction fraction, is calculated according to the formula $$O_2ER = VO_2/DO_2$$

Advantageously, the microprocessor 15 comprises means adapted to calculate the quantity DO$_2$/V'CO$_2$ML, the ratio between the amount of conveyed oxygen DO$_2$ and the amount of carbon dioxide removed by the oxygenator V'CO$_2$ML. This ratio is particularly useful in case of CPB treatments, wherein the amount of carbon dioxide removed by the oxygenator V'CO$_2$ML corresponds to the amount of total removed carbon dioxide inasmuch as the patient is bypassed and does not therefore make any contribution to the elimination of the carbon dioxide from the blood, where it provides an important parameter in identifying the presence of any kidney problems in the patient.

The device 1 comprises at least one sensor 21, 22, 23 inserted in a point of the external cardiovascular supporting circuit 2, suitable for the continuous measurement of the blood pressure, and comprises a sensor 24 suitable for the continuous measurement of the lactates. The sensor 24 can also be defined: lactate sensor.

More specifically, the device 1 comprises at least two sensors, identified with reference numerals 21 and 22, installed in distant points of the circuit 2, and the relative data appear in the two boxes at the lower edge of the display 16 marked as P$_{IN}$ and P$_{OUT}$. The sensors 21 and 22 are arranged on opposite sides of the oxygenator 4, so that the quantity P$_{IN}$ corresponds to the pressure at the blood inlet port to the oxygenator 4, while the quantity P$_{OUT}$ corresponds to the pressure at the blood outlet port from the oxygenator 4. The sensors 21 and 22 can also be referred to as the inlet pressure sensor and the outlet pressure sensor, respectively.

Further calculated is the quantity known by the acronym ΔP relating to the difference between the two pressure values P$_{IN}$ and P$_{OUT}$ detected by the sensors 21 and 22.

In the case of ECMO or ECLS treatments, the device 1 comprises a further sensor 23 installed along the venous line 3, upstream of the pump 5, adapted to detect the value of the blood suction pressure by the pump itself, identified by the code P$_{drain}$. The sensor 23 can also be defined: suction pressure sensor.

In the case instead of CPB treatments, the device 1 comprises a sensor, indicated by reference numeral 27 in FIG. 1, for the measurement of the patient's average pressure PMP. The sensor 27 can also be defined: average pressure sensor.

Such sensor 27 is of the type of a pressure transducer which is applied to the patient in order to detect the patient's blood pressure, and therefore both the systolic and the diastolic pressure. The sensor 27 is operationally connected to the microprocessor 15, which is programmed to calculate the patient's average pressure PMP on the basis of an algorithm of a type known to the technician in the field. For example, the microprocessor 15 is adapted to calculate the average pressure PMP on the basis of the maximum and minimum pressures detected by the sensor 27 in a predefined time interval.

The sensors 23 and 27 are therefore alternative to each other depending on the type of treatment carried out.

The functioning of the present invention is as follows.

Once the circuit 2 has been connected to the patient and device 1 to a power supply, it is possible to proceed with the extracorporeal circulation to support the patient.

With extracorporeal circulation, monitoring also begins thanks to the transmission of data to the microprocessor 15 by all the sensors described above.

At a certain point of operation, the display will show the instantaneous values of the various quantities detected by the sensors, updated, for example, at regular and preset time intervals.

Advantageously, the microprocessor 15 is provided with means to show on the display 16 in graphic form at least one quantity by means of a diagram of the same, represented in ordinate, as a function of time, represented in abscissa. In particular, at a certain phase the operator may be interested in knowing the trend of a particular quantity as a function of time and in this case, by pressing the relative box 17, the corresponding graph appears on the display 16.

At the same time, the microprocessor 15 proceeds to calculate the quantities V'CO$_2$ML and V'O$_2$ML.

Suitably, the device 1 also detects the amount of carbon dioxide removed from the patient's lung V'CO$_2$NL and calculates the quantity relating to the amount of total removed carbon dioxide V'CO$_{2total}$.

The graphic representation of these quantities permits providing the medical staff with immediate and easily understandable information on the patient's vital functions, i.e., on the amount of carbon dioxide removed from the same V'CO$_2$NL, and, therefore, duly regulating the oxygenator parameters in such a way that the amount of total removed carbon dioxide V'CO$_{2total}$ corresponds to the required value.

In other words, when the medical staff detect that the amount of carbon dioxide removed from the patient V'CO$_2$NL has increased over time, which corresponds to an improvement in the patient's breathing capacity, they make adjustments on the oxygenator 4 so as to reduce the amount of carbon dioxide removed from the same. Similarly, when the medical staff detect that the amount of carbon dioxide removed from the patient V'CO$_2$NL has dropped over time, which corresponds to a worsening of the patient's breathing capacity, they make adjustments on the oxygenator 4 so as to increase the amount of carbon dioxide removed by the same to compensate for the deficit which has occurred. The medical staff continue to adjust the oxygenator 4 as described above until the patient's lung capacity reaches self-sufficiency.

It has in practice been ascertained that the described invention achieves the intended objects and, in particular, the fact is underlined that the graphic representation relating to the amount of carbon dioxide removed by the oxygenator and to the amount of oxygen transferred by the oxygenator, enables the medical staff to have immediate and intuitive information on the operation of the oxygenator and on how extracorporeal circulation is proceeding.

In particular, the numerical and/or graphic representation of the quantity relating to the amount of carbon dioxide removed from the patient and the amount of total removed carbon dioxide allow the medical staff to keep the overall situation of extracorporeal circulation under control.

The invention claimed is:

1. A device for the continuous monitoring of blood characteristic quantities in an external cardiovascular supporting circuit, said circuit including a venous line which conveys blood from the patient to an oxygenator, and along which at least one pump is arranged, and an arterial line which returns blood from the oxygenator to the patient, where said oxygenator comprises at least one blood inlet port connected to said venous line and at least one blood outlet port connected to said arterial line, at least one inlet channel and at least one outlet channel of a work gas intended to supply oxygen to the blood and/or to remove carbon dioxide from the same, the device comprising:
    a first sensor connected to the venous line and a second sensor connected to the arterial line suitable for the continuous measurement of the quantities consisting of venous saturation (SAT V) of oxygen and of arterial saturation (SAT A) of oxygen, respectively;
    at least a third sensor inserted along said venous line and suitable for the continuous measurement of the quantity constituted by the flow of blood (Qb) sent by said pump to the oxygenator;
    at least a fourth sensor inserted in a point of the external cardiovascular supporting circuit and suitable for the measurement of the quantity constituted by the hemoglobin (Hb);
    data entering means by the operator;
    an electronic control unit provided with a microprocessor and operationally connected to a display, said microprocessor being adapted to receive the data measured by said first, second, third and fourth sensors and the data entered by the operator to make them appear at least partially on said display;
    at least a fifth sensor inserted in a point of the external cardiovascular supporting circuit and suitable for the continuous measurement of the flow of work gas (G$_f$);
    at least one capnometer inserted in a point of the external cardiovascular supporting circuit and adapted to measure the concentration of carbon dioxide in the blood;
        wherein said microprocessor is provided with means adapted to calculate the quantity relating to the amount of carbon dioxide removed by the oxygenator (V'CO$_2$ML) and the quantity relating to the amount of oxygen transferred by the oxygenator (V'O$_2$ML),
        and wherein said microprocessor is programmed to display in numerical form on the display the values of all the quantities measured and calculated and in graphic form at least some of said values
        wherein said device comprises:
        an acquisition means for acquiring the quantity relating to the amount of carbon dioxide removed from the patient's lung (V'CO$_2$NL) and by the fact that said microprocessor is provided with means adapted to calculate the quantity relating to the amount of total removed carbon dioxide (V'CO$_{2total}$).

2. The device according to claim 1, wherein said microprocessor comprises means adapted to calculate the quantity relating to the ratio (CO$_2$RNL) between the amount of carbon dioxide removed from the patient's lung (V'CO$_2$NL) and the quantity relating to the amount of total removed carbon dioxide (V'CO$_{2total}$).

3. The device according to claim 1, wherein said acquisition means for acquiring the quantity relating to the flow rate of blood supplied by the patient (C.O.).

4. The device A according to claim 3, wherein said acquisition means for acquiring the quantity relating to the amount of carbon dioxide removed from the patient's lung (V'CO$_2$NL) and said acquisition means for acquiring the quantity relating to the flow rate of blood supplied by the patient (C.O.) are selected from the group comprising: said data entering means and automatic detection means.

5. The device according to claim 4, wherein said device comprises at least one forced ventilation line of the patient connected to at least one pulmonary ventilator and by the fact that said automatic detection means for automatically detecting the amount of carbon dioxide removed from the patient's lung (V'CO$_2$NL) comprise said pulmonary ventilator.

6. The device according to claim 4, wherein said automatic detection means for automatically detecting the flow rate of blood supplied by the patient (C.O.) comprise at least a sixth sensor positioned on the patient him/herself.

7. The device according to claim 1, wherein said device comprises at least a seventh sensor inserted in a point of the external cardiovascular supporting circuit, suitable for the continuous measurement of the blood pressure.

8. The device according to claim 1, wherein said microprocessor comprises means adapted to calculate at least one of the quantity relating to the amount of conveyed oxygen ($DO_2$) and the quantity relating to the amount of consumed oxygen ($VO_2$).

9. The device according to claim 8, wherein said microprocessor comprises means adapted to calculate the ratio ($DO_2/V'CO_2ML$) between the quantity relating to the amount of conveyed oxygen and the quantity relating to the amount of carbon dioxide removed by the oxygenator ($V'CO_2ML$).

10. The device according to claim 1, wherein said device comprises at least an eighth sensor inserted in a point of the external cardiovascular supporting circuit, suitable for the continuous measurement of the lactates.

\* \* \* \* \*